United States Patent [19]

Gray et al.

[11] Patent Number: 5,879,939
[45] Date of Patent: Mar. 9, 1999

[54] ISOLATION OF CELLS FROM ORGAN TISSUE USING SONICATION

[75] Inventors: Brad Gray, Huntington Beach; Monty Kahn Baird, Garden Grove; Francis Lamberti, Irvine, all of Calif.

[73] Assignee: Neocrin Company, Irvine, Calif.

[21] Appl. No.: 442,587

[22] Filed: May 17, 1995

[51] Int. Cl.$^6$ .................................................... C12N 5/00
[52] U.S. Cl. ..................... 435/379; 435/325; 435/378; 435/380; 435/381
[58] Field of Search ................ 514/44, 2; 435/240.1, 435/252.3, 235.1, 325, 378, 379, 380, 381; 424/209.1, 93.1, 93.21

[56] References Cited

U.S. PATENT DOCUMENTS 4,868,121  9/1989  Scharp et al. ............................ 435/268

OTHER PUBLICATIONS

Kakizoe et al. Isolation of transitional epitelial cells from the rat urinary bladder. Investigative Urology, vol. 15, pp. 242–244, Nov. 1977.
Cecil Textbook of Medicine. Wyngaarden et al. ed., 19th edition, vol. 2, Apr. 6, 1993.
Harrison's Principles of Internal Medicine. Isselbacher et al. ed., 13th edition, 1994.
Ballinger, WF and Lacy, PE, "Transplantation of Intact Pancreatic Islets in Rats," Surgery 72:175–186 (1972).
Horagushi and Merrell, Diabetes 30:455–58 (1982).
Scharp, World Journal of Surgery 8:143–51 (1984).
Scharp, et al., Surgery 102:869–79 (1987).
Kilburn, DG, et al., "Enhanced sedimentation of mammalian cells following acoustic aggregation," Biotechnol. Bioeng. 34:559–62 (1989).
Crouse, CA, et al., "Extraction of DNA from forensic–type sexual assault specimens using simple, rapid sonication procedures," BioTechniques 15:641–42, 644–48 (1993).
Gray et al., Arch Surg., 114, 1979, 96–99.
Smyk, Exp. Biol. and Medicine, 1977, 84.
K.A. Heald et al., "Isolation of islets of Langerhans from the weanling pig," *Diabetes Res*, 17:7–12 (1991).
P. Altieri et al., "Purification of proteinase free collagenase from commercial batches of the enzyme," *Prep. Biochem*, 20:137–144 (1990).

M.D. Bond et al., "Purification and separation of individual collagenases of *Clostridium histolyticum* using red dye ligand chromatography," *Biochem*, 23:3077–3085 (1984).
M.D. Bond, "Purification, Characterization and Relationship between the different individual collagenases of *Clostridium Histolyticum*," Ph.D. Thesis 1983, Florida State University College of Arts and Science.
G.H.J. Wolters et al., "An Anlaysis of the role of collagenase and protease activity in the enzymatic dissociation of the rat pancreas for islet isolation," *Dibetologia*, 35:735–742 (1992).
G.H.J. Wolters et al., "Factors Influencing the Isolation Process of Islets of Langerhans," Department of Surgery, University of Groningen, Groningen, The Netherlands.
G. Villani et al., "Optimization of the Use of Collagenase in Porcine Islet Isolation," Transplantation Proceedings, 26:1125–1126, No. 3, Jun. (1994).
G. Wolters et al., "Different Roles Of Class I And II Clostidium Histolyticum Collagenase in Rat Pancreatic Islet Isolation," *Diabetes*, 44:227–233 (1995).
T. Cavanagh e tal., "Collagenase Selection," *Pancreatic Islet Transplantation*, 1:39–51 (1994).
S. Williams et al., "Collagenase Lot Selection And Purification For Adipose Tissue Digestion," *Cell Transplantation*, 4:281–289, No. 3 (1995).
J.C. Gerlach et al., "Comparison Of Four Methods For Mass Hepatocyte Isolation From Pig and Human Livers," *Transplantation*, 57:1318–1322, No. 9, May (1994).
A. Lazer et al., "Formation Of Porcine hepatocyte Spheroids For Use In A Bioartificial Liver," *Cell Transplantation*, 4:259–268, No. 3 (1995).

*Primary Examiner*—Deborah Crouch
*Assistant Examiner*—Deborah J.R. Clark
*Attorney, Agent, or Firm*—Lyon & Lyon LLP

[57] ABSTRACT

A method for isolating specific viable cell types from surrounding organ tissue is provided. The method entails the use of sonication in conjunction with tissue dissociating agents to free the cells of interest. A specific application of the method is the isolation of the insulin producing tissue of the pancreas, the islets of Langerhans. The method results in a high yield of islets that maintain a high level of viability.

33 Claims, No Drawings

ISOLATION OF CELLS FROM ORGAN TISSUE USING SONICATION

BACKGROUND

Islet Isolation

The insulin producing tissue of the pancreas, the islets of Langerhans, constitutes between about one and two percent of the mass of the pancreas. The isolation of the islets from the remainder of the pancreatic tissue is desirable for laboratory purposes and for transplantation purposes. Transplantation of islets is looked to as a possible treatment for diabetes. Transplanting islets rather than an intact pancreas or pancreatic segments offers several advantages, including the ease of transplantation, the possibility of in vitro treatment to prevent rejection without immunosuppression, the elimination of the pancreatic exocrine function (the secretion of digestive substances from the host tissue), the possibility of cryopreservation of the tissue for subsequent use, and the possibility of xenografts.

In an early method of islet separation, chopped pancreatic fragments are mixed with collagenase and incubated at 37° C. (reviewed in Scharp, World Journal of Surgery 8:143–151 (1984)). The collagenase breaks down or digests the pancreatic tissue, freeing the islets. The collagenase also acts on the islets, so that the islets released early in the process are broken down into single cells. If the process is stopped to protect the islets released early, many islets remain trapped in pancreatic fragments. Therefore only a fraction of the available intact islets are released by this method. This process is particularly ineffective for the isolation of islets from the pancreata of large animals such as humans, dogs, or pigs.

Laboratory islet isolation from rodent pancreata was greatly improved by the discovery that mechanical distension of rodent pancreata increased islet yield by causing mechanical separation of islets from the pancreas tissue. After distension the pancreas is chopped for collagenase digestion. The beneficial effect of this same type of mechanical distension has also been noticed in large animals.

Horaguchi and Merrell, Diabetes 30:455–58 (1982) developed a method for perfusing the dog pancreas with collagenase via the pancreatic duct. Subsequently, a process involving ductal distension of the pancreas with a solution containing collagenase was developed (U.S. Pat. No. 4,868,121; incorporated herein by reference). Inflation or distension of the pancreas is believed to cause some mechanical rupturing of the exocrine tissue or partial separation of the islets from the exocrine tissue, making subsequent collagenase digestion easier.

Sonication

Sound waves have been used in the past to aggregate cells and to disrupt cells. For example, ultrasound has recently been used to aggregate cells as a purification procedure. Kilburn, DG, et al., "Enhanced sedimentation of mammalian cells following acoustic aggregation," Biotechnol.Bioeng. 34:559–62 (1989). In this procedure, cells which are not sufficiently heavy to precipitate out of solution are caused to aggregate by exposure to ultrasound. The aggregates then precipitate out of the solution. This procedure uses a standing wave to aggregate the cells, and the procedure is performed in an echo chamber to create and maintain the standing wave.

Ultrasound has also long been used to disrupt cells. For example, exposure of cells to ultrasound is used to lyse the cells to isolate the nucleic acid contained inside. Crouse, CA, et al., "Extraction of DNA from forensic-type sexual assault specimens using simple, rapid sonication procedures" BioTechniques 15:641–42,644–48 (1993). This procedure uses very concentrated sound waves to disrupt the cell structure. The ultrasonic field is applied at a localized spot, such as a microtip of an emitter.

SUMMARY OF THE INVENTION

The present invention is an improvement on the process for isolating cells, such as islets of Langerhans, which incorporates sonication of the organ, such as the pancreas, as a method for dissociating the cells from other non-desired tissue. The inventors have discovered that sonication of the pancreas in conjunction with collagenase treatment results in a high degree of dissociation of the islet cells that maintain a high degree of integrity. The invention can be applied to the isolation of specific cell types from many different types of organs.

DETAILED DESCRIPTION OF THE INVENTION

The invention is an improved method for the isolation of specific viable cell types from surrounding organ tissue. The technique has specifically been applied to the isolation of islets of Langerhans cells from a pig pancreas as described below in the preferred embodiment. However, the invention is also applicable to the isolation of cell types from other organs and other animals (e.g., cells from organs from transgenic animals, islets from human pancreata). Other potential applications include the isolation of medullary cells from adrenal glands, and the isolation of hepatocytes from liver to be used, for example, as bioartificial liver systems. The organ is harvested and prepared as necessary, such as by removal of undesired segregated tissue or cells. The invention relies on the use of sound waves to accelerate tissue dissociation. The cells released from the dissociated tissue remain intact and viable, allowing separation of desired cells from unwanted tissue. Thus, this invention differs from the prior art wherein cells are either aggregated or disrupted. Implementation of the invention entails three steps.

(1) Treatment of the organ with tissue dissociating agents to release specific cell types from the surrounding organ tissue.

Tissue dissociating agents will typically include tissue degrading enzymes such as collagenase, trypsin, neutral protease or dispase, and other proteolytic enzymes, with the preferred embodiment demonstrating the use of collagenase. However, the tissue dissociating agents are not necessarily limited to enzymes. Other examples of tissue dissociating agents are chelating agents for the dissociation of fetal tissue. The length of time required for treatment with dissociating agents will vary depending on the type of the agent, the concentration of agent, and the temperature at which treatment is conducted. Treatment is allowed to proceed until a sufficient amount of tissue has dissociated without causing undue damage to released cells or cellular aggregates. Preferably at least 40%, more preferably at least 75%, and most preferably at least 90% of the tissue is dissociated, while less than 50%, more preferably less than 25%, and most preferably less than 10% of the cells are functionally damaged by treatment with the dissociating agents.

The preferred embodiment below describes the treatment of a pancreas via ductal distension, a method fully described in U.S. Pat. No. 4,868,121. That is a method in which the tissue dissociating effect of the treatment agent is enhanced by injection of the agent into the pancreas to cause tension that results in some mechanical rupturing of the exocrine tissue or partial separation of the islets from the exocrine tissue. However, the invention is not limited to this form of treatment. Other possible types of the treatment would include chopping the organ smaller into pieces and incubation with a tissue dissociating agent, or use of a dissociating agent with mechanical agitation such as incubation of the organ with marbles in a shaking container. In the preferred embodiment described below, enzyme treatment and sonication occur simultaneously.

(2) Sonication of the organ tissue to further enhance dissociation of the cells of interest.

The sonication step as described in the preferred embodiment was accomplished with a sonicating waterbath. However, it should be appreciated that other types of sonication methods could also be used. These would include acoustic horns, piezo-electric crystals, or any other method of generating stable sound waves, such as with sonication probes. In the preferred embodiment described below, sonication was conducted at about 43 kHz for approximately 20 minutes. Under approximately these same conditions, a sonication frequency of between about 40 kHz to 50 kHz is likely to be equally effective. However, a fairly wide range of frequencies, from subaudio to ultrasound (between about 7 Hz to 40 MHz, preferably between 7 Hz and 20 MHz) would be expected to give sound-enhanced tissue dissociation. Additionally, variations in the type of sonication include pulsing versus continuous sonication.

The sound waves created by the sound source must be at sufficiently low power so as not to disrupt the cells being isolated. The sonication source is run at a power level of between $10^{-4}$ and about 10 watts/cm$^2$. See "Biological Effects of Ultrasound: Mechanisms and Clinical Implications," National Council on Radiation Protection and Measurements (NCRP) Report No. 74, NCRP Scientific Committee No. 66: Wesley L. Nyborg, chairman; 1983; NCRP, Bethesda, Md. The sonicating water bath discussed above works at about 0.9 watt/cm$^2$.

The tissue to be sonicated is present in a container which will hold the tissue and dissociated cells in a fluid and which is transparent to ultrasound waves. To avoid contamination of the tissue and cells, a closed container is preferred. Additionally, use of a light-transparent container will allow visual monitoring of the progress of dissociation. Further, use of a malleable container will allow tactile monitoring. In the preferred embodiment, a self-sealing polyethylene bag is used as the container for the organ that is placed in the sonicating water bath. Other types of enclosed malleable containers could also be used, or other containers such as a plastic beaker. The frequency and power of the sonication can be adjusted to accommodate significant changes in the type of container, the volume of buffer, or in the mass of material being sonicated.

Further, the conditions for sonication are such that a standing wave is not created. In the preferred embodiment described herein, the chamber of the sonicating water bath has rounded edges so as not to create a standing wave. Additionally, presence of the irregularly shaped, acoustically dense organ or tissue in the device impedes the production of a standing wave. Thus, according to the invention, the device for delivery of the sound waves, in combination with the tissue or organ to which the sound waves are being applied, are preferably configured to avoid the production of a standing wave.

It should be appreciated that the invention encompasses the use of these steps in other orders, such as partially overlapping of steps one and two, or tissue digestion prior to sonication.

(3) Separation of the dissociated cells from other organ tissue.

Finally, once the cells of interest have become dissociated from the surrounding organ tissue by treatment with dissociating agents and sonication, they must be separated from the other organ tissue. There are a wide variety of techniques that can be used to accomplish this step. These include various techniques for mechanical disruption of the tissue such as aspiration through needles, maceration, and/or filtration. Such techniques for mechanical disruption are preferably accompanied by a concentration/purification step such as either centrifugation or use of a density gradient flush-out to separate the desired cells from the remaining tissue when the cells have a different density. Islets can be separated in this manner from other denser acinar tissue. The islet cells are then typically further purified using standard density gradient methods such as Percoll® (a colloidal PVP coated silica, available from Sigma) or Ficoll® (a non-ionic synthetic polymer of sucrose, available from Sigma) gradients. See Ballinger, WF and Lacy, PE, "Transplantation of Intact Pancreatic Islets in Rats," Surgery 72:175–186 (1972), which is incorporated herein by reference.

DETAILED DESCRIPTION OF THE PREFERRED EMBODIMENT

Isolation of Islets of Langerhans Cells From a Pig Pancreas

The pancreas is removed from the pig carcass, preferably within 10 minutes after the pig is killed. This is accomplished by cutting across the neck of the pancreas to separate the splenic and non-splenic lobes. Preferably only the splenic lobe is used for islet isolation. External fat, connective tissue and blood vessels are trimmed from the pancreas. The pancreas is placed in cold physiologic solution supplemented with 10% horse serum, such as EuroCollins, and maintained preferably at about 4° C. for preservation. The pancreas may be stored in this manner for as long as 4–6 hours prior to the islet isolation process. If the pancreas is held at a higher temperature, the pancreas should be used in a shorter period of time to avoid tissue and cellular degradation. The pancreas can be partially distended by infusion of cold physiologic solution supplemented with 10% horse serum immediately upon removal from the animal. For example, 60 mls. of Eurocollins or M199 supplemented media can be inserted through the pancreatic duct via a catheter prior to placement of the organ in the bath for storage or transport.

The splenic lobe is cannulated, preferably with a 20 gauge angiocatheter inserted into the pancreatic duct, and sutured in place. A collagenase (Boehringer Mannheim) solution containing between about 0.5 to 6.0 mg/ml (2 mg/ml is preferred) collagenase in physiologic solution (same as above) is prepared and preheated to a temperature between about 20° C. and 38° C. (37° C. is preferred). The solution is injected into the pancreatic duct of the pancreas via the angiocatheter to inflate and distend the pancreas, using between about 0.5 to 3.0 mls of solution per gram of organ (1.5 to 2 mls of solution per gram of organ is preferred). Leaks are sutured or clamped, such as with a hemostat.

The inflated pancreas is placed in a self-sealing polyethylene bag (Ziploc®) containing approximately 100 ml. of collagenase solution similar to that injected into the pancreatic duct. The self-sealing bag is sealed after expelling most of the air from the container, and the container is placed in an ultrasonic water bath, preheated and maintained at a temperature between about 20° C. and 38° C. (37° C. is preferred). The ultrasound is turned on at a frequency of about 43 kHz, and the bag is allowed to incubate with occasional agitation and visual inspection to observe the digestion process. After about 10 minutes, when the organ begins to acquire a "cracked appearance," the organ is removed from the water bath and the excess collagenase solution is drained and replaced with an equal volume of fresh warmed collagenase solution. By "cracked appearance" is meant that the lobes appear to subdivide into smaller, distinguishable acinar structures. The organ is then returned to the ultrasonic water bath and allowed to incubate for approximately 10 to 15 more minutes with occasional agitation and visual inspection to observe the digestion process. The sonication in this preferred embodiment is in a Fischer Scientific Solid State Ultrasonic FS28 water bath, with a sonication frequency of approximately 43 kHz.

At the end-point of the digestion, the organ is removed from the water bath and placed on a horizontal plate shaker, preferably with a ribbed surface. Shaking is initiated and the organ is gently dispersed in the bag by pressing the organ against the ribbed surface of the plate shaker using a light finger pressure. The tissue is poured through a stainless steel screen (nominal mesh size of 350–500 µm) and collected in a stainless steel pan partially filled with rinse medium, and further washed with approximately 4 liters of 10% horse serum supplemented, modified M199 with an additional 20 mM $CaCl_2$. Alternatively, the excess fluid can be decanted from the settled tissue in the bag, followed by resuspension of the tissue in a large volume of chilled physiologic medium inside the bag. The fluid and tissue can then be poured through the screen.

The tissue fragments collected in the pan are transferred to a collection vessel stored on ice. The process of rinsing and sieving tissue fragments away from the digested organ on the screen is continued until no further tissue fragments are released (approximately 10 minutes). Typically about 10–60% of the initial organ mass remains as undigested tissue.

The islet cells are then typically further purified using standard density gradient methods such as Percoll® or Ficoll® gradients (Scharp et al., 1987, Surgery 102:869–79). For example, the pooled islets are suspended in Ficoll® plus sodium diatrizoate (Sigma) at a density of 1.120 gm/ml and further purified and concentrated by density gradient centrifugation through a 1.060 to 1.180 Ficoll®/sodium diatrizoate gradient. This process typically yields between 500 to 2000 islet equivalent numbers per gram of organ mass, with purities and viabilities greater than 75%.

Table 1 shows islet yield from five different isolations utilizing the process of the invention. Pig pancreases were treated as described above. Islets were tested for viability and purity. Viability averaged 82%; purity averaged 96%.

TABLE 1

| Lot Number | % Digested | Pre-Purification Islet Number | Pre-Purification Equivalent Islet Number (EIN) | Post-Purification Islet Number | Post-Purification Equivalent Islet Number (EIN) | Viability | Purity |
|---|---|---|---|---|---|---|---|
| 5009-001 | 51 | 156,240 | 41,244 | 119,280 | 36,053 | 80 | 99 |
| 5011-003 | 61 | ND | N/A | 170,246 | 81,133 | 52 | 99 |
| 5012-002 | 53 | 278,880 | 77,448 | 336,560 | 152,611 | 90 | 82 |
| 5017-001 | 29 | 130,480 | 38,528 | 47,040 | 46,497 | 100 | 100 |
| 5018-003 | 34 | 178,080 | 49,194 | 113,680 | 51,033 | 87 | 98 |

"Percent Digested" is the ratio of (initial organ mass less remaining organ mass)/(initial organ mass). "Islet Number" refers to the number of cell clusters stained with DTZ (dithiozone), a zinc-binding dye which detects insulin. "Equivalent Islet Number," or "EIN," provides a volume corrected number of full sized islets represented by the stained clusters. EINs can be compared for determining maintenance or breakdown of original islet structure and for determining volume of islets before and after the procedure.

Viability is measured by fluorescein diacetate and ethidium bromide staining. The fluorescein diacetate stains living cells, while the ethidium bromide detects non-living cells. Purity is measured by DTZ binding by counting the positively stained cells divided by total particles in a particular volume.

Three thousand EIN each from lot numbers 5017-001 and 5018-003 were implanted into STZ-diabetic athymic mice. These islets were able to reduce blood glucose levels from greater than 500 mg/dl to less than 200 mg/dl in both cases. Thus, the isolated islets are functional—both glucose responsive and insulin producing.

Table 2 shows insulin content of islets isolated in three batches by the methods of the invention.

TABLE 2

| Lot Number | Insulin Content per islet (ng/islet) |
|---|---|
| NP097-4320-005 | 2.2 |
| NP097-4361-001 | 11.0 |
| NP097-5005-001 | 11.7 |

Variations of the elements of the invention will be apparent to those skilled in the art, and it is intended that this invention be limited only by the scope of the appended claims.

We claim:

1. A method for isolating viable cells from organ tissue which has been removed from the body comprising the steps of:
   a. treating the organ tissue with a solution containing a tissue dissociating agent;
   b. sonicating the organ tissue by supplying soundwaves in an energy range between $10^{-4}$ watt/$cm^2$ and 10 watts/$cm^2$, the sonication being performed while the organ tissue is being treated with the solution containing the tissue dissociating agent such that more than about 50% of the cells are viable; and c. separating viable released cells of interest from other organ tissue.

2. The method of claim 1 wherein the organ tissue is selected from the group consisting of an intact organ, organ segments, and partially dissociated organ tissue.

3. The method of claim 1 wherein the tissue dissociating agent is selected from the group consisting of tissue degrading enzymes and chelating agents.

4. The method of claim 3 wherein the tissue degrading enzyme is selected from the group consisting of collagenase, trypsin, neutral protease, and dispase.

5. The method of claim 1 wherein the sonication is conducted in a frequency range of 7 Hz to 40 MHz.

6. The method of claim 5 wherein the sonication is conducted in a frequency range of 7 Hz to 20 MHz.

7. The method of claim 1 wherein the soundwaves are supplied by a sonicating water bath.

8. The method of claim 7 wherein the sonication is conducted in the frequency range of 40 kHz to 50 kHz.

9. The method of claim 1 wherein the tissue dissociating agent is collagenase.

10. The method of claim 9 wherein the soundwaves are supplied in the range of 7 Hz to 40 MHz.

11. The method of claim 10 wherein the soundwaves are supplied in the range of 7 Hz to 20 MHz.

12. The method of claim 1 wherein the organ is selected from the group consisting of pancreas, liver, and adrenal gland.

13. The method of claim 2 wherein the organ is selected from the group consisting of pancreas, liver, and adrenal gland.

14. The method of claim 1 wherein the organ is from a transgenic animal.

15. The method of claim 1 wherein the soundwaves are supplied at between 0.1 watt/cm$^2$ and 1.0 watt/cm$^2$.

16. A method for isolating viable islets of Langerhans from pancreatic tissue which has been removed from the body comprising the steps of:

a. treating the pancreatic tissue with a solution comprising pancreatic tissue degrading enzymes;

b. sonicating the pancreatic tissue by supplying soundwaves having an energy range of between 10$^{-4}$ watt/cm$^2$ to 10 watts/cm$^2$, wherein the treating step and the sonicating step at least partially overlap (such that more than 50% of cells are viable); and c. separating released viable islets of Langerhans from other pancreatic tissue.

17. The method of claim 16 wherein the pancreatic tissue is selected from the group consisting of a whole pancreas, segments of a pancreas and partially dissociated pancreas.

18. The method of claim 10 wherein said treating step further comprises ductal distension with the solution comprising pancreatic tissue degrading enzymes.

19. The method of claim 16 wherein the pancreatic tissue is treated with collagenase.

20. The method of claim 16 wherein the soundwaves are supplied by a sonicating water bath.

21. The method of claim 20 wherein the sonicating water bath emits soundwaves in a frequency range of 40 kHz to 50 kHz.

22. The method of claim 16 wherein the soundwaves are supplied at between 0.1 watt/cm$^2$ and 1.0 watt/cm$^2$.

23. The method of claim 16 wherein the pancreatic tissue is selected from a group consisting of human pancreatic tissue and pig pancreatic tissue.

24. The method of claim 16 wherein the pancreatic tissue is from a transgenic animal.

25. A method for isolating viable islets of Langerhans from a mammalian pancreas which has been removed from the body comprising the steps of:

a. subjecting the mammalian pancreas to ductal distension with a solution containing collagenase;

b. sonicating the mammalian pancreas by applying soundwaves in an energy range of 10$^{-4}$ watts/cm$^2$ to 10 watts/cm$^2$ to the mammalian pancreas while the mammalian pancreas is in the presence of the solution containing collagenase (such that more than about 50% of the cells are viable); and c. separating released viable islets of Langerhans from other mammalian pancreatic tissue.

26. The method of claim 25 wherein the solution containing collagenase has a collagenase concentration of between about 0.5 mg/ml and 6.0 mg/ml.

27. The method of claim 25 wherein said sonicating step is accomplished by means of a sonicating water bath.

28. The method of claim 27 wherein the sonicating water bath in said sonicating step is maintained at a temperature between about 20° C. and 38° C.

29. The method of claim 25 wherein the soundwaves are supplied in the range of 7 Hz to 40 MHz.

30. The method of claim 29 wherein the soundwaves are supplied in the range of 7 Hz to 20 MHz.

31. The method of claim 30 wherein the soundwaves are supplied in the range of 40 kHz to 50 kHz.

32. The method of claim 25 wherein the soundwaves are in the energy range of between 0.1 watt/cm$^2$ and 1.0 watt/cm$^2$.

33. The method of claim 25 wherein the mammalian pancreas is from a transgenic animal.

* * * * *